United States Patent
Hufford et al.

(10) Patent No.: US 12,263,043 B2
(45) Date of Patent: *Apr. 1, 2025

(54) METHOD OF GRAPHICALLY TAGGING AND RECALLING IDENTIFIED STRUCTURES UNDER VISUALIZATION FOR ROBOTIC SURGERY

(71) Applicant: Asensus Surgical US, Inc., Durham, NC (US)

(72) Inventors: Kevin Andrew Hufford, Durham, NC (US); David J Meagher, Durham, NC (US)

(73) Assignee: Asensus Surgical US, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/480,321

(22) Filed: Oct. 3, 2023

(65) Prior Publication Data

US 2024/0024064 A1 Jan. 25, 2024

Related U.S. Application Data

(63) Continuation of application No. 17/499,822, filed on Oct. 12, 2021, now Pat. No. 11,771,518, which is a continuation of application No. 16/018,037, filed on Jun. 25, 2018, now Pat. No. 11,141,226.

(60) Provisional application No. 62/524,154, filed on Jun. 23, 2017, provisional application No. 62/524,143, (Continued)

(51) Int. Cl.
| | | |
|---|---|---|
| *G09G 5/00* | (2006.01) | |
| *A61B 1/00* | (2006.01) | |
| *A61B 34/00* | (2016.01) | |
| *A61B 34/10* | (2016.01) | |
| *A61B 90/00* | (2016.01) | |
| *G06T 7/00* | (2017.01) | |
| *G06T 7/40* | (2017.01) | |
| *G06T 7/50* | (2017.01) | |

(Continued)

(52) U.S. Cl.
CPC ...... *A61B 90/361* (2016.02); *A61B 1/000094* (2022.02); *A61B 1/0005* (2013.01); *A61B 1/00055* (2013.01); *A61B 34/10* (2016.02); *A61B 34/25* (2016.02); *G06T 7/0012* (2013.01); *G06T 7/40* (2013.01); *G06T 7/50* (2017.01); *G06T 7/90* (2017.01); *G06T 11/00* (2013.01); *A61B 2034/105* (2016.02); *A61B 2034/254* (2016.02); *G06T 2207/10068* (2013.01); *G06T 2210/41* (2013.01); *G06T 2210/62* (2013.01)

(58) Field of Classification Search
CPC ......... G06T 19/006; G06T 19/00; G06T 7/74; G06T 7/94; G06T 11/00; G06T 2207/10012; G06T 2207/20021; G06F 3/011; G06F 3/012; G06F 3/04815; G02B 27/017; G02B 1/041; G02B 2027/0178; H04L 67/52; H04N 7/152; G06V 20/20
USPC ......................................................... 345/633
See application file for complete search history.

(56) References Cited

U.S. PATENT DOCUMENTS

| | | | |
|---|---|---|---|
| 2007/0156017 A1* | 7/2007 | Lamprecht | ......... A61B 1/00194 600/102 |
| 2016/0113728 A1* | 4/2016 | Piron | ..................... A61B 34/30 606/130 |
| 2016/0239967 A1* | 8/2016 | Chou | ....................... G06T 7/11 |

* cited by examiner

Primary Examiner — Gordon G Liu

(57) ABSTRACT

A system and method for augmenting an endoscopic display during a medical procedure including capturing a real-time image of a working space within a body cavity during a medical procedure. A feature of interest in the image is (Continued)

identified to the system using eye tracking input, and a graphical tag is displayed on the image marking the feature.

13 Claims, 4 Drawing Sheets

Related U.S. Application Data filed on Jun. 23, 2017, provisional application No. 62/524,133, filed on Jun. 23, 2017.

(51) Int. Cl.
*G06T 7/90* (2017.01)
*G06T 11/00* (2006.01)

FIG. 4
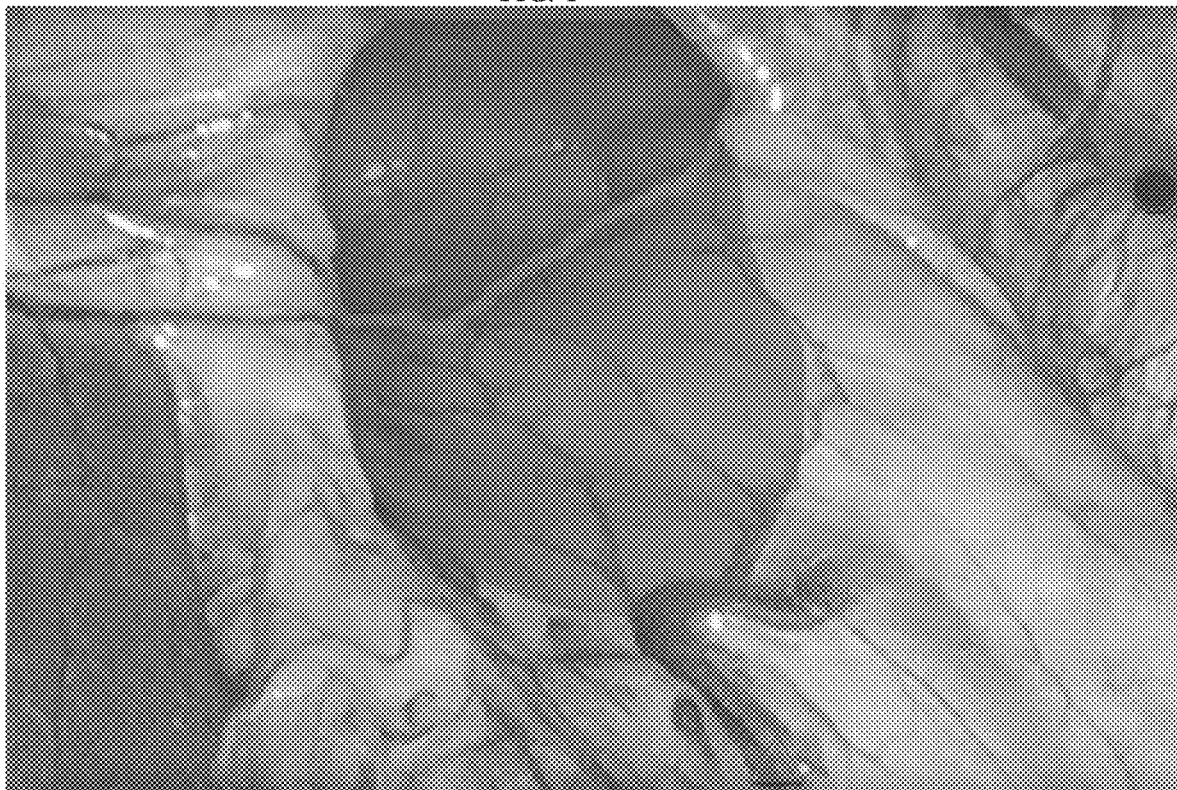
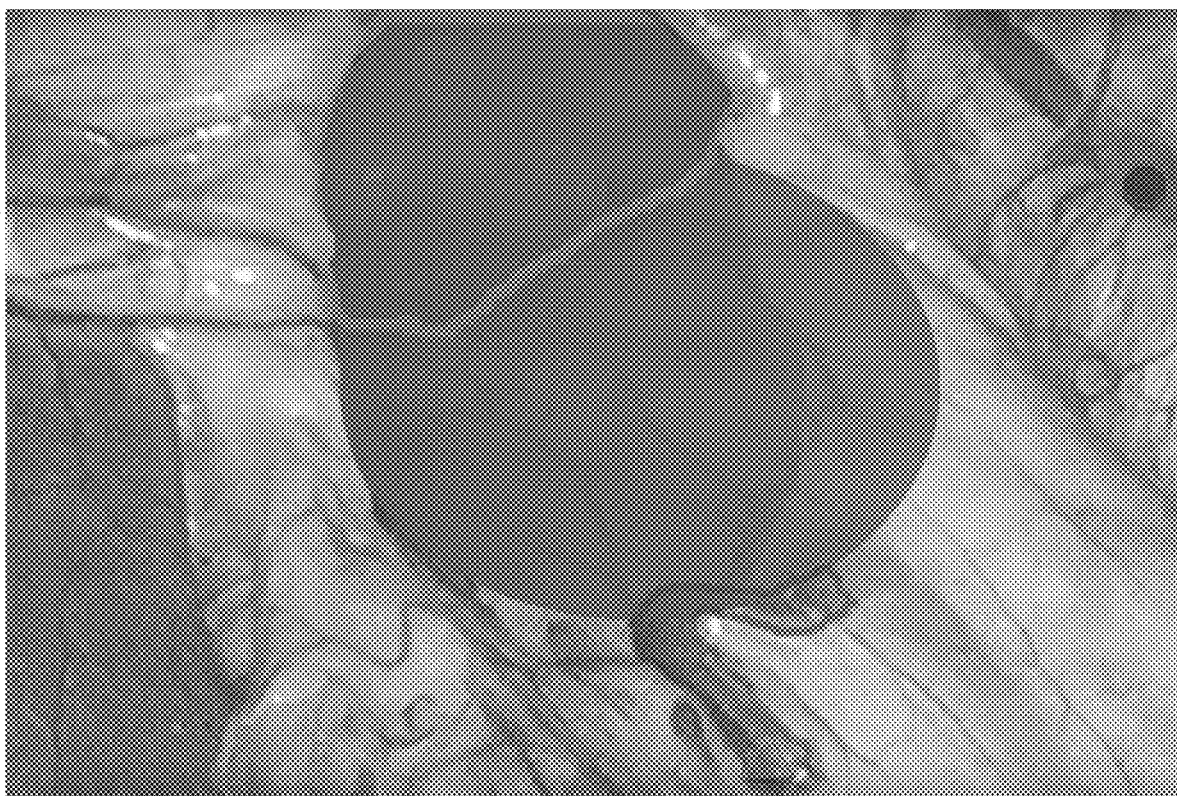
FIG. 5

METHOD OF GRAPHICALLY TAGGING AND RECALLING IDENTIFIED STRUCTURES UNDER VISUALIZATION FOR ROBOTIC SURGERY

This application is a continuation of U.S. application Ser. No. 17/499,822, filed Oct. 12, 2021, which is a continuation of U.S. application Ser. No. 16/018,037, filed Jun. 25, 2018 which claims the benefit of Provisional No. U.S. Provisional 62/524,133, filed Jun. 23, 2017, U.S. Provisional 62/524,143, filed Jun. 23, 2017, and U.S. Provisional 62/524,154, filed Jun. 23, 2017, each of which is incorporated herein by reference.

BACKGROUND

There are different types of robotic systems on the market or under development. Some surgical robotic systems, such as those described in U.S. Pat. Nos. 8,506,555, 9,358,682, and 9,707,684 use a plurality of robotic arms. Each arm carries a surgical instrument, or the endoscopic camera used to capture images from within the body for display on a monitor. Other surgical robotic systems use a single arm that carries a plurality of instruments and a camera that extend into the body via a single incision. See WO 2016/057989. Each of these types of robotic systems uses motors to position and/or orient the camera and instruments and to, where applicable, actuate the instruments. Typical configurations allow two or three instruments and the camera to be supported and manipulated by the system.

The image captured by the camera is shown on a display at the surgeon console. The console may be located patient-side, within the sterile field, or outside of the sterile field.

As with manual laparoscopic surgery, surgical instruments and cameras used for robotic procedures may be passed into the body cavity via trocars. Input to the system is generated based on input from a surgeon positioned at the console, typically using input devices such as input handles and a foot pedal. US Published Application 2013/0030571 describes the use of an eye tracking system to give input to the system. The input is used to control motion of the camera-holding arm, allowing repositioning of the camera (e.g. to pan and/or zoom the image seen by the user on the image display) based on the where the user is looking on the camera display and/or how close the user's eyes are to the display.

Motion and actuation of the surgical instruments and the camera is controlled based on the user input. Some robotic systems are configured to deliver haptic feedback to the surgeon at the controls, such as by causing the surgeon to feel resistance at the input handles that is proportional to the forces experienced by the instruments moved within the body.

In a robotic surgical system utilizing endoscopic visualization, it would be advantageous for the surgeon to dynamically tag or "bookmark" single points or identified anatomical structures in the surgical space for the purposes of recalling and monitoring their positions visually at a later time. This would allow the surgeon to better navigate the surgical space under compromised visual conditions (caused by blood, smoke, or other types of obstructions) by locating or possibly avoiding critical anatomical structures. This data may be used to create a "world model" for a surgical robotic system and be used to identify structures in the abdomen that are to be avoided by robotically controlled instruments. Such a system, which may include configurations that anticipate the possibility of instrument contact with such structures as well as those that cause the robotic system to automatically avoid the structures, is described in co-pending U.S. application Ser. No. 16/010,388, which is incorporated herein by reference.

Various surface mapping methods exist that allow the topography of a surface to be determined and can be implemented for use in surgical applications. Some such methods use stereoscopic information from a 3D endoscope, structured light measured by a 3D endoscope, structured light measured by a 2D endoscope, or a combination thereof. One type of surface mapping method is one using structured light. Structured light techniques are used in a variety of contexts to generate three-dimensional (3D) maps or models of surfaces. These techniques include projecting a pattern of structured light (e.g. a grid or a series of stripes) onto an object or surface. One or more cameras capture an image of the projected pattern. From the captured images the system can determine the distance between the camera and the surface at various points, allowing the topography/shape of the surface to be determined. Other types of surface mapping methods also exist and may be used in conjunction with the system and method described in this application. These types of techniques may be implemented in the systems and processes described below.

BRIEF DESCRIPTION OF THE DRAWINGS

FIGS. 2-6 show endoscopic views of a surgical field illustrating use of the features described in this application, in which:

FIG. 2 shows the original endoscopic view at the start of a procedure;

FIG. 3 shows the view of FIG. 2, with identified structures highlighted;

FIG. 4 shows the view of FIG. 2, but with an obstruction in the imaging field partially obscuring the endoscopic view and with partial highlighting of the identified structures;

FIG. 5 shows the view of FIG. 4, but in which the amount of obstruction has increased;

FIG. 6 shows the view of FIG. 5 in which the amount of obstruction has increased to nearly full obstruction, and in which a structure to avoid is highlighted as the visual field becomes more obscured.

DETAILED DESCRIPTION

A system in accordance with the present invention includes one or more information sources, such as 2D, 3D and/or structured light imaging sources, and a visual display for displaying visual information from those sources to a user. A surgeon or other user uses an input device to identify to the system the structures, areas etc. that are to be tagged. The associated processor registers the location of the tagged structure, area etc. to a model of the surgical site within the patient and is programmed to generate overlays displayed on the visual display that identify or mark the tagged structures or areas.

Figure 1:
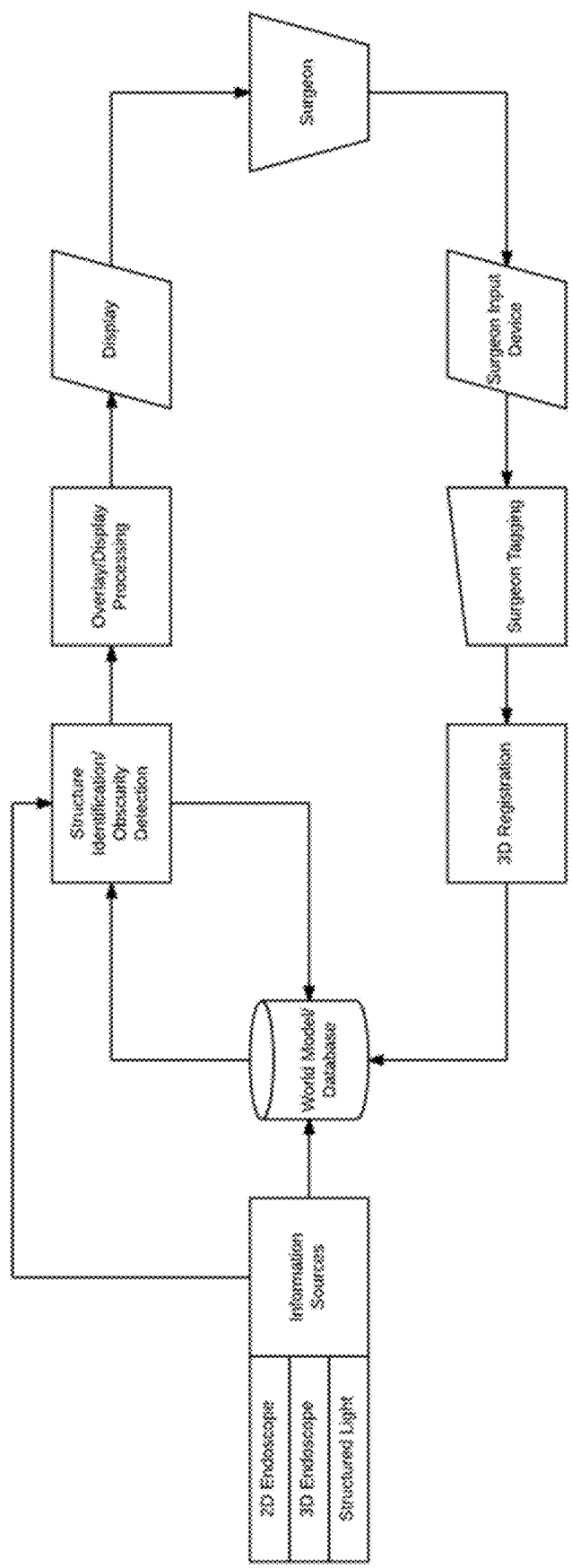
FIG. 1 schematically illustrates information flow for the methods of tagging structures and providing overlays.

FIG. 1 schematically illustrates information flow for the methods of tagging structures and providing overlays. Note that not all information sources listed are necessary for use of the invention, and additional information sources may be used without departing from the scope of the invention. At a high level, this application describes a system and method for visually tracking locations or structures within a surgical endoscopic visual field of view as that view changes. The system acquires data from one or more sources and builds an internal topographical model of the surgical space which allows the surgeon to tag, mark, flag, or bookmark structures or locations in the visual field utilizing that model. Some implementations allow the surgeon to recall previously tagged structures or locations via the robotic user interface, and overlay a graphical tag over the selected location in the endoscopic view to facilitate navigation of the surgical space under compromised visual conditions.

In this application, the term "tag" is used to refer to a tag, bookmark (an alternative term is "waypoint), and may be any of the following:
  Point, pose
  2-dimensional surface, 3-dimensional surface
  Region
  Edge The 3-dimensional data defining the tissue topography and the data corresponding to the position/location of the tags (tagged locations/identified structures) may be gathered from stereoscopic information from a 3D endoscope, structured light measured by a 3D endoscope, structured light measured by a 2D endoscope, or a combination thereof. This 3-dimensional data may be acquired as described in co-pending application U.S. Ser. No. 16/018,039, filed Jun. 25, 2018, entitled Method and Apparatus for Providing Procedural Information Using Surface Mapping. The 3-dimensional data may be acquired once during a procedure, updated intermittently at a certain interval, updated intermittently on-demand, or updated continuously. The tag position data may be registered to the 3-dimensional model of the surgical anatomy comprising the system's world view. The tag and/or 3-dimensional model may be registered to the real-time endoscopic view of the surgical field.

Turning now to a discussion of the type of user input that may be given, structures or locations can be tagged in the field of view using a point and click model of selection. The user may move a graphical pointer to a target location and give input to the system to cause the system to tag the location. The user input device might be any type of device known to those skilled in the art that will allow a user to select a location or area on a screen and identify that area to the system. As one example, an eye tracking system, manual keypad control, motion of a user input handle of the surgeon console, or other input device may be used to manipulate a mouse pointer moveable on the visual display to the region the user wishes to tag. Input of the user's selection may be given using physical input (e.g. button, foot pedal), voice command, etc. As one specific example, a button on the surgeon handle can be pressed to finalize the selections. As another example, the endoscopic display may be a touch screen that allows the user to create a tag by directly touching the feature of interest on the touch screen. The selected locations in the visual field are correlated and linked to the corresponding areas of the dynamic anatomical model of the surgical space, and can be saved and recalled by the surgeon, regardless of changes to the view or the anatomical model. Some implementations allow for automatic recognition of anatomical structures selected by the surgeon using algorithms (including, without limitation, computer vision) and historical data from a variety of sources. Some implementations allow for dynamic adjustments by the surgeon to the translucence of the graphical tags based on desired visual effect.

In alternative implementations, the robotic surgical system may use kinematic knowledge from the surgical robotic system to determine the location of a tag. In such embodiments, the user might steer the instrument tip to the location to be tagged and give user input to the system instructing the system to record the data corresponding to the pose of the instrument tip (position and orientation in Cartesian space) in order to create the tag.

User input, such as in forms described here for setting tags, may also be used to instruct the system to remove selected tags, or to take some other action with respect to a selected tag. The system might also be equipped to allow a second user such as a surgical assistant, to add/remove tags, classify/categorize items in the model, etc.

Tags are visually represented on the endoscopic display using graphical overlays to mark points, boundaries, regions, sections of structures such as blood vessels, etc. This can give the surgeon the continued ability to navigate surgical instruments towards, away from or around identified features even when the surgical field is obscured by smoke, pooling blood etc. Visual characteristics of the tags may be altered as a means of visual feedback to the surgeon relating to some changed condition, such as a change in visibility in the endoscopic field that compromises the visibility of identified structures on the endoscopic display. Thus, for example, the opacity of an overlay may be changed, such as by a change in its opacity or color as the identified structure becomes less visible or changes. As a more specific example, the opacity of the overlay might be increased as the identified structure becomes less visible on the endoscopic image. A decrease in the visibility of an identified structure might additionally or alternatively result in a visual, auditory or haptic notification signal to the user.

The system may be set up to recognize that a tagged/bookmarked structure is visually obscured and to provide/alter the visual feedback to the surgeon as described in the preceding paragraph. The system may thus be able to detect changes in the visibility of bookmarked features on the endoscopic view (or increases in the degree to which the bookmarked features are obscured). This may be carried out using, edge detection techniques (e.g. detecting edges of a forming blood pool), by detecting changes in image contrast (e.g. local contrast or color or overall contrast or color), or by detecting changes in the image texture. Detected changes in measured depth and/or local surface contours might also be used.

Overlays can be provided to the display by an external processor as an integrated signal, or by a display that integrates multiple signals—such as from an endoscope and a graphics generator—into a single display to the user.

The robotic surgical system may be responsive to the tags in a variety of ways. The position of a tag may be used as a reference with respect to which one or more of the robotic arms is repositioned and/or reoriented in order to reposition/reorient a surgical instrument or camera. The surgeon input controls might include an input device allowing the surgeon to instruct the robotic system to automatically move an attached instrument to a given location and/or orientation that is defined relative to the location of a tag (rather than requiring the surgeon to navigate the surgical instrument to/towards the tag). This is particularly beneficial in instances where some of the endoscopic view is obscured by blood, smoke etc. Thus the instrument tip may be automatically moved to the location of a tag, or to a predetermined standoff distance (optionally in a predetermined standoff direction) in response to input to the robotic surgical system to robotically position the instrument tip as instructed. The position of a tag may be similarly used in a step for automatically repositioning and/or reorienting the endoscope.

As another example, the location of a tag may be used as the basis for controlling the maximum insertion depth of at least one instrument carried by a robotic arm. In other words, the location data corresponding to the tag position is used to establish a plane beyond which the instrument tip should not pass. Should the user attempt to navigate the instrument tip beyond that plane, one or more of a number of events might take place. For example, the robotic arm may stop moving so it does not pass the plane, the user might be provided with visual or auditory feedback that the instrument tip has reached the plane, the user might be provided with haptic feedback in the form of vibratory feedback or force feedback giving the user the sensation of pushing the instrument tip against a barrier. Similar forms of feedback might additionally or alternatively be given as the system detects movement of the instrument within a certain distance of the plane, with the magnitude of the feedback (volume or pitch of auditory feedback, intensity or frequency of vibratory feedback, brightness, size or other appearance feature of visual feedback) increasing as the instrument tip moves closer to the plane.

The system may be set up to provide the user with menus that allow categorization of tags into groups such as "structures to avoid", "targeted structures", "paths to follow", etc. Concepts described here might be implemented in an augmented reality configuration with overlays displayed on a headset or transparent head mounted device.

Co-pending U.S. application Ser. No. 16/010,388 filed Jun. 15, 2018, describes creation, and use of a "world model", or a spatial layout of the environment within the body cavity, which includes the relevant anatomy and tissues/structures within the body cavity that are to be avoided by surgical instruments during a robotic surgery. The systems and methods described in this application may provide 3D data for the world model or associated kinematic models in that (see for example FIG. 5 of that application) type of system and process. For example, the inputs, outputs, and outcomes referenced in the co-pending application may be used in concert with the bookmarking techniques described in this current application. In addition, the automatic or assisted detection of obstructions (e.g. pooled blood or an expanding region of pooling blood) or other anatomical structures/features described here may be incorporated into the world model and/or into scans generated in co-pending U.S. application Ser. No. 16/018,042 entitled Method and Apparatus for Providing Improved Peri-operative Scans and Recall of Scan Data, filed Jun. 25, 2018, which is incorporated herein by reference.

It also should be noted that 3-dimensional data acquired as described in co-pending application U.S. Ser. No. 16/018,039, filed Jun. 25, 2018, entitled Method and Apparatus for Providing Procedural Information Using Surface Mapping and data acquired in co-pending U.S. application Ser. No. 16/018,042 entitled Method and Apparatus for Providing Improved Peri-operative Scans and Recall of Scan Data, filed Jun. 25, 2018 may be used in conjunction with, or without, the 3D data described using the system disclosed herein, to provide 3D data for the world model or associated kinematic models in system and process described in co-pending U.S. application Ser. No. 16/010,388 filed Jun. 15, 2018.

Usage Example

During a surgical procedure, the surgeon identifies an area of the anatomy of critical importance such as a major artery, or a ureter, or other feature. The surgeon then engages the robotic user interface to enter location selection mode. Once in selection mode, the surgeon points to the feature of interest on the endoscopic display. This pointing step may be carried out by navigating a graphical pointer to the feature of interest using input from a user input device, which in this example is an eye tracker. Using eye tracking technology, the user can perform this step by moving his/her eyes to the region of interest and then instructing the system using another input mechanism such as a button or foot pedal to mark the region of interest. More particularly, using the example of the eye tracking technology, the surgeon navigates the graphical mouse pointer to the feature of interest, places the mouse pointer over the endoscopic view of the major artery and "selects" it using a button on the robotic handle interface or other input devices. Location selection mode is exited and the graphical mouse pointer is removed from the view. For the remainder of the surgery, a graphical "tag" is unobtrusively visible on top of the major artery identified by the surgeon in the endoscopic view, regardless of changes in the view or obstructions to the view such as blood or smoke. In the event that the major artery is obscured by another anatomical structure, the tag changes its visual representation (translucence, color, etc.) to indicate that the identified structure is no longer in the foreground ("buried"). A mechanism is also provided to allow the surgeon to remove and restore the graphical tag from view at any time during the procedure.

Figure 2:
Figure 3:
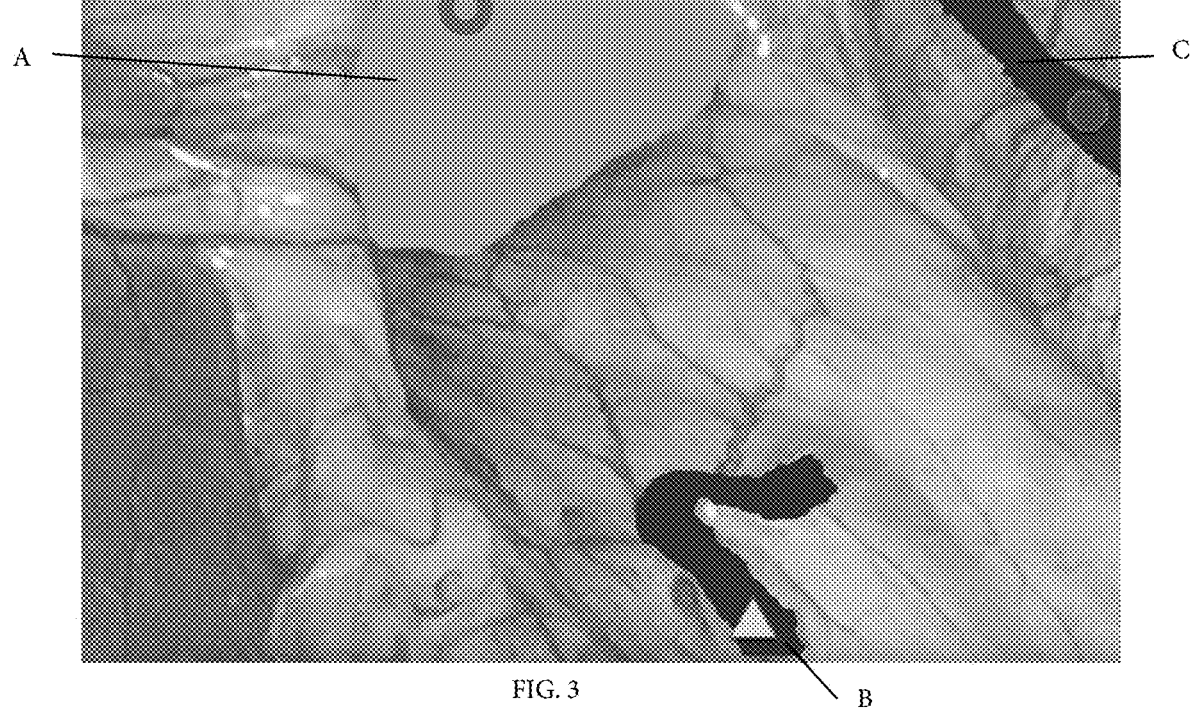
Figure 6:
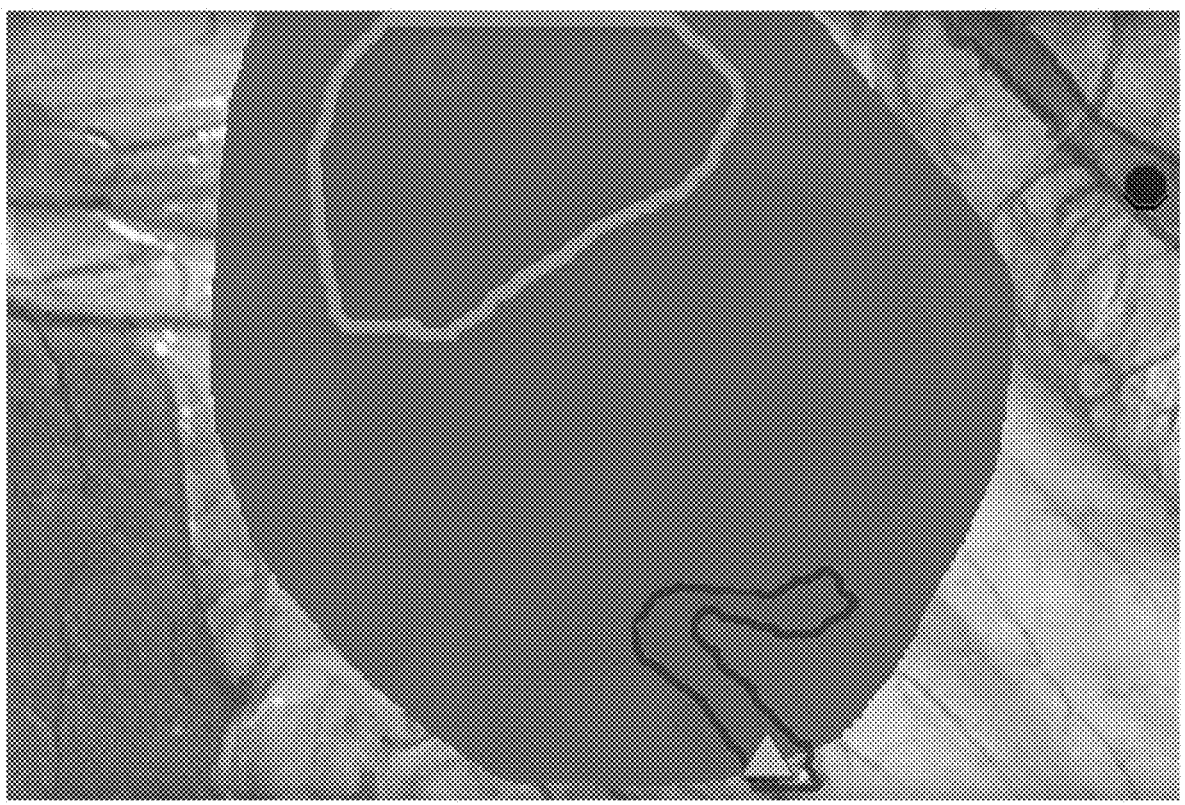

Another usage example shown in the series of figures attached as FIG. 2-6. FIG. 2 shows the initially clear endoscopic view. In FIG. 3, structures or regions A, B and C have been marked with color overlays. Here the overlay is shown as fully opaque, but under normal operation, would be transparent or nearly so, and/or it might display only perimeters of the identified structures. This figure shows both varying icons and highlighted regions to denote different structure types/categories or regions, but either method may be used and is within the scope of the invention. In this example, region A may signify an area for operation into which the surgeon may want to enter. The highlighted perimeter in the visually-obscured space may allow the surgeon to be aware of its boundaries, either to enter it with increased assurance of its location, or to avoid pushing too hard against the perimeter of it. Regions B and C may be vessels that the surgeon wishes to avoid with the surgical instruments. In FIG. 4, blood has begun to fill the surgical field, and the initially clear endoscopic view has become partially obscured by blood. The perimeters marking the regions A, B and C, as well as the shape remain displayed. Note that this view also shows the partial highlighting of the identified structures. FIGS. 5 and 6 are endoscopic views so progressively increasing levels of occlusion of the view by the blood pool, with FIG. 6 showing almost full occlusion of some identified structures and highlighting of the identified structures. Note that a structure to avoid is highlighted, or its highlighting is further enhanced, as the visual field becomes more obscured to assist the surgeon in avoiding it while attempting to stop the blood loss. As the field fills with blood, the highlight around the blood vessels marked by regions B and C may allow the surgeon to find it in the obscured field and provide clamping pressure/cauterization/etc. to stop the bleeding.

All patents and applications referred to herein are incorporated herein by reference.

We claim:

1. A method of tagging regions of interest on displayed images during a medical procedure, comprising:
    positioning an endoscope in a body cavity;

positioning a surgical instrument in the body cavity;

capturing images of a surgical site within the body cavity and displaying the images on a display, the displayed images including images of the surgical instrument, displaying a graphical pointer as an overlay on the images displayed on the display, receiving input from an eye tracker in response to a user directing the user's gaze towards the displayed images, in response to a user directing the user's gaze towards a first region of the surgical site as displayed in the displayed images, positioning the graphical pointer at the first region; and in response to user selection input, displaying a graphical tag at the first region of the displayed images.

2. The method of claim 1, wherein the method further comprises entering a tag selection mode comprising, wherein the steps of displaying the graphical pointer, positioning the graphical pointer, and displaying the graphical tag are performed in the tag selection mode.

3. The method of claim 2, wherein the method further comprises:
exiting the tag selection mode, wherein graphical tag remains displayed at the region of interest on images of the surgical site displayed on the display.

4. The method of claim 1, wherein the method further includes removing the graphical tag in response to user input to remove the tag.

5. The method of claim 4, wherein the method further includes restoring the graphical tag at the region of interest in response to user input to restore the tag.

6. The method of claim 1, wherein the selection input is sound input.

7. The method of claim 1, wherein the selection input is received from at least one of a button, foot pedal, joystick, stylus, or touch input.

8. The method of claim 1, further including:
mounting the surgical instrument to a first robotic manipulator arm;
causing the first robotic manipulator arm to manipulate the surgical instrument within the body cavity in in response to user manipulation of a user input handle; and
causing the first robotic manipulator to move the surgical site towards a region of the surgical site corresponding to the tagged first region.

9. The method of claim 8, further comprising causing the first robotic manipulator to move a tip of the first surgical instrument to a location a predetermined standoff distance from the tagged first region.

10. The method of claim 9, further including:
mounting the endoscope to a second robotic manipulator arm; and
causing the second robotic manipulator to move the endoscope towards the tagged first region.

11. The method of claim 1, wherein the tagged first region has a depth, and wherein the method further comprises:
mounting the surgical instrument to a first robotic manipulator arm;
causing the first robotic manipulator arm to manipulate the surgical instrument within the body cavity in in response to user manipulation of a user input handle; and
preventing movement of the first instruments to a location in the body cavity that is deeper than the depth.

12. The method of claim 1, further comprising:
detecting in real-time a change in the image during the medical procedure, the change indicative of the feature of interest becoming at least partially obscured by smoke or pooling blood; and
altering a quality of the displayed graphical tag to enhance its visibility in response to the detected change.

13. The method of claim 1, wherein the surgical instrument is an endoscope.

* * * * *